United States Patent [19]

Prossel et al.

[11] Patent Number: 5,648,528
[45] Date of Patent: Jul. 15, 1997

[54] SATURATED FLUOROALKYLAMINES AND THEIR DERIVATIVES, AND MIXTURES THEREOF

[75] Inventors: Günter Prossel; Wolfgang Knaup; Frank Wehowsky, all of Burgkirchen, Germany

[73] Assignee: Hoechst Aktiengesellschaft, Germany

[21] Appl. No.: 476,725

[22] Filed: Jun. 7, 1995

Related U.S. Application Data

[62] Division of Ser. No. 208,004, Mar. 9, 1994, abandoned.

[51] Int. Cl.⁶ .................................................. C07C 229/00
[52] U.S. Cl. .................................................. 562/574
[58] Field of Search ........................... 562/574; 564/261

[56] References Cited

U.S. PATENT DOCUMENTS

| | | | |
|---|---|---|---|
| 3,535,381 | 10/1970 | Hauptschein et al. | 260/570.9 |
| 4,012,437 | 3/1977 | Shachat et al. | 260/482 R |
| 4,059,629 | 11/1977 | Foulletier et al. | 260/583 |
| 4,183,367 | 1/1980 | Goebel et al. | 132/7 |
| 4,430,272 | 2/1984 | Ehrl et al. | 260/501.12 |
| 4,853,141 | 8/1989 | Durual et al. | 252/51 |
| 4,859,357 | 8/1989 | Germanaud et al. | 252/51 |
| 5,240,990 | 8/1993 | Kallfass et al. | 524/714 |

FOREIGN PATENT DOCUMENTS

| | | |
|---|---|---|
| 2198788 | 3/1989 | Australia . |
| 57925 | 8/1982 | European Pat. Off. . |
| 296046 | 12/1988 | European Pat. Off. . |
| 296935 | 12/1988 | European Pat. Off. . |
| 0 311 473 | 4/1989 | European Pat. Off. . |

*Primary Examiner*—Brian M. Burn
*Attorney, Agent, or Firm*—Connolly & Hutz

[57] ABSTRACT

New saturated fluoroalkylamines and carboxyalkylbetaines and alkylsulfobetaines derived therefrom, and mixtures containing the new fluoroalkylamines and mixtures containing the new fluorobetaines are described. The saturated fluoroalkylamines conform to the formula below

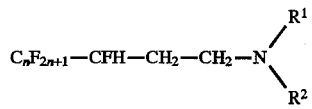

in which n is an integer from 3 to 17 and $R^1$ and $R^2$ are $C_1$ to $C_4$-alkyl, $C_1$ to $C_4$-hydroxyalkyl or hydrogen, with the proviso that only one of the two substituents $R^1$ and $R^2$ is hydrogen. The carboxyalkylbetaines and sulfobetaines and the mixtures thereof are highly effective products for reducing the surface tension of water/air systems and the interfacial tension of water/hydrocarbon systems.

2 Claims, No Drawings

SATURATED FLUOROALKYLAMINES AND THEIR DERIVATIVES, AND MIXTURES THEREOF

This is a division of my application Ser. No. 08/208,004, filed Mar. 9, 1994 now abandoned.

DESCRIPTION

The invention relates to saturated fluoroalkylamines and to the corresponding carboxyalkylbetaines and sulfobetaines. The invention also relates to mixtures comprising these new fluoro compounds.

Saturated and unsaturated fluoroalkylamines are valuable starting materials for the preparation of cationic or amphoteric fluoroalkyl compounds such as fluoroalkylbetaines, which represent surfactants with numerous possible uses, for example as agents for lowering the surface tension of water (water/air) or the interfacial tension of water/hydrocarbon systems.

For instance, U.S. Pat. No. 3,535,381 describes unsaturated fluoroalkylamines of the formula $R_f$—CF=CH—$CH_2$—NZ in which $R_f$ is a perfluoroalkyl radical and NZ is the radical of a primary or secondary amine. They are prepared by reacting a fluoroalkylethylene with a primary or secondary amine, as indicated by the following equation.

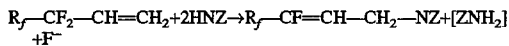

Their quaternary ammonium compounds are said to have a good activity in lowering the surface tension of water.

In U.S. Pat. No. 4,059,629, saturated fluoroalkylamines of the formula $R_f$—$(CH_2)_m$—NZ, in which $R_f$ and NZ have the definitions indicated and m is 2 or 4, and mixtures comprising these saturated and the abovementioned unsaturated fluoroalkylamines are recommended as agents for lowering the surface tension of water.

Finally, U.S. Pat. No. 4,183,367 describes carboxyalkylbetaines containing a saturated fluoroalkyl group, and U.S. Pat. No. 4,430,272 describes alkylsulfobetaines containing an unsaturated fluoroalkyl group, as effective surfactants.

The present invention now provides new saturated fluoroalkylamines, and alkylsulfobetaines and carboxyalkylbetaines derived from these fluoroalkylamines, and mixtures containing the new fluoroalkylamines and mixtures containing the new fluorobetaines.

The saturated fluoroalkylamines according to the invention conform to the formula (1) below

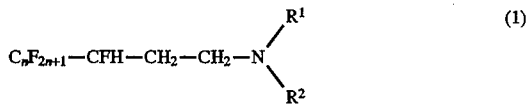

in which n is an integer from 3 to 17, preferably from 5 to 13, and $R^1$ and $R^2$ are $C_1$ to $C_4$-alkyl, $C_1$ to $C_4$-hydroxyalkyl or hydrogen, with the proviso that only one of the two substituents $R^1$ and $R^2$ is hydrogen.

The perfluoroalkyl radical $C_nF_{2n+1}$ may be straight-chain or branched but is preferably straight-chain. In the case of a branched perfluoroalkyl group, terminal branching is preferred. Examples which can be mentioned are $C_3F_7$, $C_5F_{11}$, $C_7F_{15}$, $C_9F_{19}$ and $C_{11}F_{23}$ and mixtures of perfluoroalkyl homologs having the given meaning of n, for example $C_5F_{11}$ to $C_{11}F_{23}$ mixtures ($C_5F_{11}/C_{11}F_{23}$). $R^1$ and $R^2$, which are preferably methyl or ethyl, may be identical or different. The hydroxyalkyl group is preferably —$CH_2CH_2$—OH.

The saturated fluoroalkylamines of the formula (1) according to the invention are prepared by hydrogenating fluoroalkenylamines of the formula (1a) below

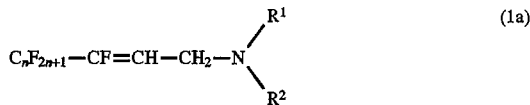

in which n, $R^1$, $R^2$ and the perfluoroalkyl radical are as defined, in the presence of a catalyst from the group comprising ruthenium, rhodium, palladium, osmium, iridium and platinum and at a temperature of from 0° to 50° C., preferably from 15° to 30° C. The unsaturated fluoroalkylamines (1a) to be employed are known and are described in detail in U.S. Pat. No. 3,535,381 which was mentioned in the introduction. Using the combination according to the invention of a hydrogenation catalyst from the group of the platinum metals and a specific hydrogenation temperature, selective hydrogenation of the —CF=CH— group to —CFH—$CH_2$— is achieved, and the saturated fluoroalkylamine (1) desired is obtained in a high yield. The pressure in the reaction of fluoroalkenylamine of the formula (1a) with hydrogen may vary within wide limits; the critical factor is the use of the stated noble metal catalysts in combination with the stated temperature. Using a high hydrogen pressure (in comparison with a low hydrogen pressure) reduces the necessary hydrogenation time. With regard to an economical hydrogenation time, it has proven advantageous to maintain a hydrogen pressure of from 20 to 150 bar, preferably from 70 to 110 bar. The end of the reaction with hydrogen (about 1 mol of hydrogen is required per mole of fluoroalkenylamine) is indicated by constant pressure being reached. The hydrogenation time is generally from 1 to 4 hours and depends essentially on the hydrogenation temperature, the hydrogen pressure and the quantity of catalyst. The stated catalysts from the group of the platinum metals, from which palladium and platinum are preferred, can be employed as such or in the form of supported catalysts, the support material being composed, for example, of alumina, silica gel, kieselguhr or pumice. The catalyst is employed in a quantity of from 0.005 to 0.5% by weight, preferably in a quantity of from 0.01 to 0.1% by weight, these percentages by weight being based on the weight of the unsaturated fluoroalkylamine to be hydrogenated (the percentages by weight relate to the stated elements and thus do not include the support material). The exothermic hydrogenation according to the invention can be carried out with or without the use of a solvent. A solvent will be employed in particular should the fluoroalkenylamine to be hydrogenated be solid at the chosen hydrogenation temperature. Preferred organic solvents to give a liquid phase are the lower alkanols, such as methanol, ethanol, propanol and/or isopropanol. The solvent is generally employed in a quantity such that the concentration of the solution of fluoroalkenylamine in the solvent is from approximately 10 to 70% by weight, preferably from 30 to 50% by weight. On conclusion of the hydrogenation, which is carried out in liquid phase, the saturated fluoroalkylamine of formula (1) is present. If it is desired to separate off the catalyst employed to obtain a catalyst-free fluoroalkylamine, this can be achieved by, for example, decanting or filtering. In order to purify the product further, it is possible to wash it once or more with water and in addition, if desired, to distil it. The saturated fluoroalkylamines according to the invention, with the special γ-CFH— unit are obtained in a high yield and purity. They are liquid at room temperature, except for those having a particularly long perfluoroalkyl group. They are more stable to heat and pH than the unsaturated starting fluoroalkylamines and are thus stable on storage, even over a prolonged period. They represent advantageous starting compounds (intermediates) for the preparation of new carboxyalkylbetaines and alkylsulfobetaines and of new mixtures comprising the saturated fluoroalkylamines according to the invention.

The carboxyalkylbetaines according to the invention conform to the formula (2) below

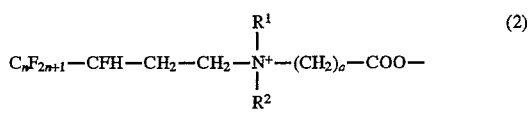

in which a is 1, 2, 3 or 4, preferably 1, and n, $R^1$ $R^2$ and the perfluoroalkyl radical are as defined for formula (1).

The carboxyalkylbetaines according to the invention are prepared by carboxyalkylation of compounds of the formula (1). The betainizing agent or alkylating agent employed is a halocarboxylic acid of the formula (2) a below

in which X is a halogen, preferably Cl or Br, and a is as defined, or a salt thereof, preferably an alkali metal salt, or a $C_1$ to $C_4$-alkyl ester of this halocarboxylic acid. If a halocarboxylic ester is used, then clearly the alkylation product is to be subjected to hydrolysis in order to obtain the compound of the formula (2). The betainization is preferably carried out at a temperature of from 60° to 100° C., preferably from 70° to 95° C., and in the presence of a solvent from the group of the lower alkanols or water or mixtures of water and lower alkanols such as methanol, ethanol, propanol and/or isopropanol (preferably in a volume ratio of 1 part water to from 10 to 30 parts alkanol). The solvent is employed in a quantity such that the concentration of the fluoroalkylamine solution present is from 20 to 70% by weight, preferably from 30 to 50% by weight. The betainization of the tertiary fluoroalkylamine stoichiometrically requires 1 mol of halocarboxylic acid, ester compound or halocarboxylic salt per mole of fluoroalkylamine. Therefore, in order to achieve a maximum degree of betainization, from 1 to 1.1 mol, preferably from 1 to 1.03 mol, of betainizing agent are employed per mole of tertiary fluoroalkylamine. The pH of the reaction mixture is in general from 5 to 8, preferably from 6.5 to 7.5. The reaction which proceeds at atmospheric pressure or at a more or less slight overpressure is generally continued until all of the tertiary fluoroalkylamine has been betainized. If alkylation is carried out using a halocarboxylic acid, the hydrohalic acid formed is preferably bound with an alkali metal hydroxide to give the alkali metal halide. The alkali metal hydroxide (NaOH or KOH) is preferably employed in the form of a 30 to 60% by weight strength aqueous solution. Working up the resulting solution of γ-CFH—carboxyalkylbetaines of the formula (2), for example by distilling off the solvent to obtain solid carboxyalkylbetaines, is often completely unnecessary, since for many applications even the solutions can be used.

The alkylsulfobetaines according to the invention conform to the formula (3) below

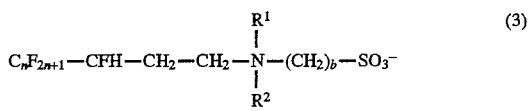

in which b is 1, 2, 3 or 4, preferably 3 or 4, and n, $R^1$, $R^2$ and the perfluoroalkyl radical are as defined for formula (1).

The alkylsulfobetaines according to the invention are prepared by sulfoalkylation of compounds of the formula (1). The sulfoalkylating agent employed is a sultone of the formula (3a) below

in which b is as defined, preferably propanesultone or butanesultone. The sulfoalkylation is carried out in the presence of an organic solvent which is inert with respect to the reactants. Examples of suitable solvents are methanol, ethanol, butylglycol, butyldiglycol or acetone. The advantageous reaction temperature is in the range from 50° to 100° C., the reaction taking place under essentially unpressurized conditions. At these temperatures the duration of the sulfoalkylation is between 1 and 10 hours. The sultones should advantageously not be employed in a proportion above that required by stoichiometry, since they are toxic. When the sulfoalkylation has ended the γ-CFH—alkylsulfobetaines of the formula (3) can be obtained in solid form by distilling off the solvent. For many applications, however, even the resulting solutions of the new sulfobetaines can be employed.

The carboxyalkylbetaines and sulfobetaines according to the invention having the particular feature of —CFH—in the fluoroalkyl radical have extraordinary surfactant properties. They bring about an unexpectedly large reduction in the surface tension of water/air systems and in the interfacial tension of water/hydrocarbon systems, the use of only very small quantities often being sufficient.

The mixtures of saturated fluoroalkylamine compounds according to the invention essentially comprise
A) from 60 to 90% by weight, preferably from 75 to 85% by weight, of at least one saturated fluoroalkylamine of the given formula (1) and
B) from 10 to 40% by weight, preferably from 15 to 25% by weight, of at least one saturated fluoroalkylamine of the formula (4) below

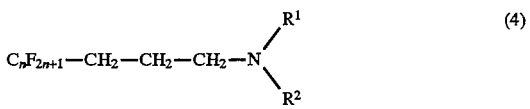

in which n, $R^1$ $R^2$ and the perfluoroalkyl radical are as defined for formula (1), percentages by weight being based on the weight of the mixture.

The mixtures of saturated fluoroalkylamines of the formulae (1) and (4) according to the invention are prepared by hydrogenating fluoroalkenylamines of the abovementioned formula (1a) in the presence of a catalyst from the group comprising iron, cobalt and nickel and at a temperature of from 0° to 50° C., preferably from 15 to 30° C. Using the combination according to the invention of a hydrogenation catalyst from the iron group and a specific hydrogenation temperature, the hydrogenation of compounds of the formula (1a) leads to a high yield of the mixtures described, essentially comprising the saturated fluoroalkylamines of the formulae (1) and (4). The formation of these mixtures is apparently the result of two different reaction mechanisms. The compounds of the formula (1) are apparently formed by hydrogenation of the —CF=CH— group in (1a) to give —CFH—CH$_2$— and the compounds of the formula (4) are probably formed by further hydrogenation of —CFH—CH$_2$— with the release of HF, as illustrated by the following equation:

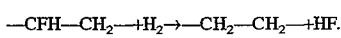

The pressure in the reaction of the fluoroalkenylamine of the formula (1a) with hydrogen can vary within wide limits, the critical factor being the use of the stated catalysts in combination with the stated temperature. Using a high hydrogen pressure requires (in comparison with a low hydrogen pressure) a shorter hydrogenation time. With respect to an economic hydrogen time, it has proven advantageous to maintain a hydrogen pressure of from 5 to 50 bar, preferably from 10 to 30 bar. The end of the reaction with hydrogen (approximately 2 mol of hydrogen are required per mole of fluoroalkenylamine) is indicated by constant pressure being reached. The hydrogenation time is generally from 1 to 4 hours and depends essentially on the hydrogenation temperature, the hydrogen pressure and the quantity of catalyst. The stated catalysts from the iron group, from which nickel is preferred, can be employed as such or in the form of supported catalysts, the support material being composed, for example, of alumina, silica gel, kieselguhr or pumice. The catalyst is employed in a quantity of from 0.005 to 0.5% by weight, preferably in a quantity of from 0.01 to 0.1% by weight, percentages by weight being based on the weight of the unsaturated fluoroalkylamine to be hydrogenated (the percentages by weight are based on the stated elements and thus do not include the support material). The strongly exothermic hydrogenation according to the invention is preferably carried out in the presence of a solvent, irrespective of whether the fluoroalkenylamine to be hydrogenated is intended to be solid or liquid at the chosen hydrogenation temperature. Preferred organic solvents to give a liquid phase are the lower alkanols, such as methanol, ethanol, propanol and/or isopropanol. The solvent is generally employed in a quantity such that the concentration of the fluoroalkenylamine in the solvent is approximately from 10 to 70% by weight, preferably from 30 to 50% by weight. On conclusion of the hydrogenation, which is carried out in liquid phase, the mixture of compounds of the formulae (1) and (4) desired is present. If it is desired to separate off the catalyst used to obtain a catalyst-free mixture, this can be achieved, for example, by decanting or filtering. The product can be purified further by washing it once or more with water, and, if desired, distilling it, preferably in the form of a steam distillation. It was found that the gels obtained during washing could be destroyed by alkalification to a pH from 8 to 10. The mixtures according to the invention of compounds of the formulae (1) and (4) are obtained in a high yield and purity. They are liquid at room temperature, except for those having a particularly long perfluoroalkyl group. They are more stable to heat and pH than the unsaturated starting fluoroalkylamines and are thus stable on storage even over a prolonged period. They represent advantageous starting compounds (intermediates), since they can be betainized to give highly effective surfactant mixtures of carboxyalkylbetaines and/or sulfobetaines.

The carboxyalkylbetaine mixtures according to the invention (mixture 1) thus comprise essentially
A) from 60 to 90% by weight, preferably from 75 to 85% by weight, of at least one carboxyalkylbetaine of the given formula (2) and
B) from 10 to 40% by weight, preferably from 15 to 25% by weight, of at least one carboxyalkylbetaine of the formula (5) below

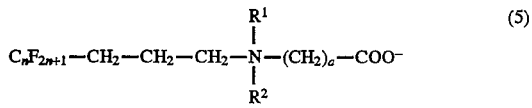

in which a, n, $R^1$ $R^2$ and the perfluoroalkyl radical are as defined for formula (2).

The sulfobetaine mixtures according to the invention (mixture 2) essentially comprise
A) from 60 to 90% by weight, preferably from 75 to 85% by weight, of at least one alkylsulfobetaine of the given formula (3) and
B) from 10 to 40% by weight, preferably from 15 to 25% by weight, of at least one alkylsulfobetaine of the formula (6) below

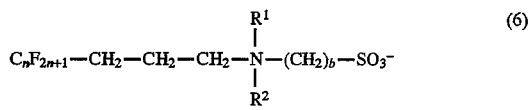

in which b, n, $R^1$, $R^2$ and the perfluoroalkyl radical are as defined for formula (3).

These surfactant mixtures according to the invention are prepared by carboxyalkylation or sulfoalkylation of the above-described mixtures of compounds of the formulae (1) and (4), with the carboxyalkylation and sulfoalkylation being carried out in each case in the same manner as described above for the compounds of the formula (1). The carboxyalkylbetaine mixtures and sulfoalkylbetaine mixtures obtained have a surprisingly high effectiveness in reducing the surface tension of water-air systems and the interfacial tension of water-hydrocarbon systems, with only very small quantities often being adequate.

The invention also relates to mixtures obtained by combination of the carboxyalkylbetaine mixture described (mixture 1) and of the alkylsulfobetaine mixture described (mixture 2). The weight ratio of mixture 1 to mixture 2 can vary within wide limits. The new mixture (mixture 3) in general essentially comprises from 20 to 80% by weight, preferably from 40 to 60% by weight, of mixture 1 and from 20 to 80% by weight, preferably from 40 to 60% by weight, of mixture 2, percentages by weight being based on the finished mixture. The components are advantageously mixed with stirring at room temperature or above, for example at from 50° to 80° C. These mixtures according to the invention of saturated fluoroalkylcarboxyalkylbetaines and saturated fluoroalkylalkylsulfobetaines are particularly surface- and interface-active. Because of a putative synergistic effect, the surface tension and interface tension values obtained are often very low, even with only a very small quantity being used.

The invention is now illustrated in more detail using examples.

Examples 1 to 5 below relate to the compounds of the formula (1) according to the invention:

EXAMPLE 1

A 300 ml autoclave was charged with 200 g of $C_5F_{11}$—CF=CH—$CH_2$—$N(CH_3)_2$ and 2 g palladium catalyst (i.e. a catalyst comprising 5% by weight of palladium on active carbon with 49% by weight of $H_2O$). The sealed autoclave was flushed with nitrogen and then with hydrogen, hydrogen was then injected up to a pressure of 80 bar, and, with shaking at from 20° to 25° C. and the continuous supplementary injection of hydrogen up to a maximum of 100 bar, hydrogenation was carried out until no more hydrogen was taken up. Constant pressure was reached after 4 hours. The autoclave was let down and opened and its contents were worked up: the catalyst was filtered off and the filtrate was distilled in vacuo. 183 g (i.e. a yield of 91% of theory) of saturated fluoroalkylamine of the formula ($C_5F_{11}$—CHF—$CH_2CH_2$—$N(CH_3)_2$ were obtained, having the following properties:

Boiling point: 58° to 59° C./15 mbar

Purity, determined by gas chromatography: 98 area-% (referred to below simply as "GC")

Amine number: 26.3

$^{13}$C-NMR (CDCl$_3$):

γ-CHF: 86.8 ppm (d, 2d); 1 J (CF)=185 Hz

β-CH$_2$: 25.8 ppm (d, t); 2 J (CF)=21 Hz

α-CH$_2$: 54.0 ppm (s)

N(CH$_3$)$_2$: 45.5 ppm (s)

EXAMPLE 2

In analogy to Example 1, using 200 g of C$_7$F$_{15}$—CF=CH—CH$_2$—N(CH$_3$)$_2$ with 4 g of palladium catalyst and a hydrogen pressure of from 80 to 100 bar at from 20° to 40° C., after 5 hours, 177 g (88% of theory) of fluoroalkylamine of the formula C$_7$F$_{15}$—CHF—CH$_2$CH$_2$—N(CH$_3$)$_2$ were obtained.

Boiling point: 83° to 85° C./15 mbar

GC: 99 area-%

Amine number: 20.9

$^{13}$C NMR: as for Example 1

EXAMPLE 3

In analogy to Example 2, using 100 g of C$_7$F$_{15}$—CF=CH—CH$_2$—N(CH$_3$)$_2$ and 1 g of ruthenium catalyst (i.e. a catalyst comprising 5% by weight of ruthenium on active carbon) in 50 ml of methanol, after a hydrogenation time of 6 hours, 74 g (74% of theory) of fluoroalkylamine of the formula (C$_7$F$_{15}$—CHF—CH$_2$CH$_2$—N (CH$_3$)2 were obtained.

Boiling point: 83° to 85° C./15 mbar

GC: 98 area-%

Amine number: 20.7

$^{13}$C NMR: as for Example 1

EXAMPLE 4

In analogy to Example 2, using 100 g of C$_7$F$_{15}$—CF=CH—CH$_2$—N(CH$_3$)$_2$ and 1 g of rhodium catalyst (i.e. a catalyst comprising 5% by weight of rhodium on Al$_2$O$_3$) in 50 ml of methanol as solvent, 64 g (64% of theory) of fluoroalkylamine of the formula C$_7$F$_{15}$—CHF—CH$_2$CH$_2$—N(CH$_3$)$_2$ were obtained.

Boiling point: 83° to 85° C./15 mbar

GC: 99 area-%

Amine number: 20.8

$^{13}$C NMR: as for Example 1

EXAMPLE 5

150 g of C$_n$F$_{2n+1}$—CF=CH—CH$_2$—N(CH$_3$)$_2$ were hydrogenated with 1.5 g of the stated palladium catalyst in 100 g of isopropanol as solvent, analogously to Example 1, at a hydrogen pressure of from 80 to 100 bar and at a temperature of from 20° to 30° C. for 4.5 hours.

For working up, the solvent was distilled off after filtration and then the hydrogenated crude amine obtained was subjected to steam distillation. 134 g of fluoroalkylamine of the formula C$_n$F$_{2n+1}$—CHF—CH$_2$CH$_2$—N(CH$_3$)$_2$ were obtained, a yield of 89% of theory.

GC: 99 area-%

Amine number: 19.7

$^{13}$C NMR: as for Example 1

The perfluoroalkyl radical C$_n$F$_{2n+1}$ is a mixture of C$_5$F$_{11}$, C$_7$F$_{15}$, C$_9$F$_{19}$ and C$_{11}$F$_{23}$.

Example 6 below relates to the compounds of the formula (2) according to the invention:

EXAMPLE 6

A 500 ml stirred apparatus (fitted with condenser, dropping funnel and thermometer) was charged with 75 g (0.15 mol) of C$_n$F$_{2n+1}$—CHF—(CH$_2$)$_2$—N(CH$_3$)$_2$, 19.5 g of sodium chloroacetate (98%, 0.16 mol) and 126 g of ethanol/H$_2$O (20:1). The reaction mixture was held at reflux (i.e. about 80° C.) with stirring for 30 hours. 2.4 g of 30% by weight strength aqueous NaOH were added over the course of the reaction. When the reaction had finished, the NaCl was substantially removed by filtering the reaction mixture over a rapid pressure filter heated to from 60 to 70° C. The filtrate was evaporated to dryness on a rotary evaporator. 82 g (i.e. a yield of 95% of theory) of carboxymethylbetaine (with a residual NaCl content of 2% by weight) of the following formula were obtained:

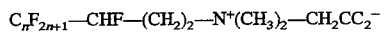

Characterization by 1H NMR (CD$_3$OD):

γ-CHF: 5.44 ppm (1H, d, m)

β-CH$_2$: 2.45 ppm (2H, m)

α-CH$_2$: 4.00 ppm (2H, m)

N (CH$_3$) $_2$: 3.36 ppm (6H, s)

CH$_2$—CO$_2^-$: 3.95 ppm (2H, s)

The perfluoroalkyl radical C$_n$F$_{2n-1}$ is a mixture of perfluorinated C$_5$, C$_7$, C$_9$ and C$_{11}$ alkyls of the following composition, in area percentages determined by gas chromatography: C$_5$:C$_7$:C$_9$:C$_{11}$=24:59:16:1.

The carboxymethylbetaine according to the invention was tested with respect to its effectiveness in lowering the surface tension of water (mN/m) in which context it was used at different concentrations (in percent by weight) in each case at 80° C. The results are summarized below:

| % by weight | mN/m |
|---|---|
| 0.1 | 14.2 |
| 0.04 | 14.3 |
| 0.02 | 14.5 |
| 0.01 | 15.1 |
| 0.005 | 17.4 |

Example 7 below relates to the compounds of the formula (3) according to the invention:

EXAMPLE 7

A 500 ml stirred apparatus (fitted with condenser, dropping funnel and thermometer) was charged with 100 g (0.216 mol) of C$_n$F$_{2n+1}$—CHF—(CH$_2$)$_2$—N(CH$_3$)$_2$ and 146 g of monoethylene glycol monobutyl ether (butylglycol) and heated to 60° C. 26.5 g (0.217 mol) of propanesultone were metered into the heated mixture, after which the reaction mixture was stirred for 1 hour at 60° C. and then for a further 5 hours at from 105° to 110° C. The reaction mixture was worked up by adding 146 g of water and stirring for 2 hours at 95° C. (hydrolysis of excess propanesultone). The sulfobetaine of the formula C$_n$F$_{2n+1}$—CHF—(CH$_2$)$_2$—N$^+$(CH$_3$)$_2$—(CH$_2$)$_3$SO$_3^-$ was obtained in a yield of 86% of theory.

The statements made in Example 6 apply to the perfluoroalkyl radical C$_n$F$_{2n+1}$.

The alkylsulfobetaine according to the invention was tested in respect of its effectiveness in lowering the surface tension of water (mN/m) in which context different concentrations (in percent by weight) were used, in each case at 60° C. The results are summarized below:

| % by weight | mN/m |
| --- | --- |
| 0.1 | 15.7 |
| 0.04 | 16.1 |
| 0.02 | 16.4 |
| 0.01 | 16.7 |
| 0.005 | 17.8 |

Examples 8 and 9 below relate to the mixtures of compounds of the formula (1) and formula (4) according to the invention:

EXAMPLE 8

Preparation of a mixture essentially comprising 85% by weight of $C_5F_{11}$—CHF—$CH_2CH_2$—$N(CH_3)_2$ and 15% by weight of $C_5F_{11}$—$(CH_2)_3$—$N(CH_3)_2$.

A 5 l shaker autoclave was charged with 2.0 kg of $C_5F_{11}$—CF═CH—$CH_2$—$N(CH_3)_2$, 400 g of isopropanol and 20 g of Raney nickel. The sealed autoclave was flushed with nitrogen and then with hydrogen, hydrogen was then injected up to a pressure of 50 bar, and, with shaking at from 20° to 40° C. and continuous supplementary injection of hydrogen up to a maximum of 50 bar, hydrogenation was carried out until no further hydrogen was taken up. Constant pressure was reached after 2 hours. The autoclave was let down and the contents were worked up: the catalyst was filtered off and the isopropanol was removed by distillation. The residue was subsequently washed with dilute alkali and then with water to neutrality. 1960 g of the abovementioned mixture according to the invention were obtained with a purity of 95% (GC). Yield: 93% of theory. Steam distillation enabled 1804 g of 98% pure product (GC) to be obtained. Further characterization by $^{13}C$ NMR ($CDCl_3$):

Component of the formula $C_5F_{11}$—CHF—$CH_2CH_2$—$N(CH_3)_2$:

γ-CHF: 86.8 ppm (d, 2d); 1 J (CF)=185 Hz
β-$CH_2$: 25.8 ppm (d, t); 2 J (CF)=21 Hz
α-$CH_2$: 54.0 ppm (s)
N ($CH_3$)$_2$: 45.4 ppm (s)

Component of the formula $C_5F_{11}$—$(CH_2)_3$—N ($CH_3$)$_2$:
γ-$CH_2$: 29.1 ppm (t); 2 J (CF)=23 Hz
β-$CH_2$: 18.8 ppm (t); 3 J (CF)=3.6 Hz
α-$CH_2$: 58.8 ppm (s)
N($CH_3$)$_2$: 45.4 ppm (s)

EXAMPLE 9

Preparation of a mixture essentially comprising 80% by weight of $C_nF_{2n+1}$—CHF—$(CH_2)_2$—$N(CH_3)_2$ and 20% by weight of $C_nF_{2n+1}$—$(CH_2)_3$—$N(CH_3)_2$.

2.0 kg of $C_nF_{2n+1}$—CF═CH—$CH_2$—$N(CH_3)_2$, 400 g of isopropanol and 20 g of Raney nickel were hydrogenated analogously to Example 8. Hydrogenation conditions: 5 hours at from 30° to 35° C. and at from 80 to 100 bar.

For working-up, the solvent was distilled off after filtration of the mixture. The residue was washed with dilute alkali and then with water to neutrality. 1890 g of the stated fluoroalkylamine mixture according to the invention were obtained with a purity of 96% (GC); yield: 91% of theory. Further characterization was made by $^{13}C$ NMR spectroscopy as in Example 1.

The perfluoroalkyl radical $C_nF_{2n+1}$ is a mixture of $C_5F_{11}$, $C_7F_{15}$, $C_9F_{19}$ and $C_{11}F_{23}$.

Examples 10 to 13 below relate to the mixtures of compounds of the formula (2) and formula (5) according to the invention:

EXAMPLE 10

Preparation of a mixture essentially comprising
80% by weight of $C_nF_{2n-1}$—CHF—$(CH_2)_2$—$N^+(CH_3)_2$—$CH_2CO_2^-$ and
20% by weight of $C_nF_{2n-}$—$(CH_2)_3$—$N^+(CH_3)_2$—$CH_2CO_2^{31}$.

A 4l stirred apparatus (fitted with condenser, dropping funnel and thermometer) was charged with 554.3 g (1.0 mol) of a mixture of 80% by weight of $C_nF_{2n+1}$—CHF—$(CH_2)_2$—$N(CH_3)_2$ and 20% by weight of $C_nF_{2n+1}$—$(CH_2)_3$—N $(CH_3)_2$, 130.8 g of sodium chloroacetate (98% strength, 1,1 mol), 1022 g of isopropanol and 100 g of water. The reaction mixture was heated at reflux (approximately 80° C.) and with stirring for 34 hours. 2.4 g of NaOH were added as a 30% by weight strength aqueous solution over the course of the reaction. When the reaction had ended, the NaCl was substantially removed by filtering over a rapid pressure filter heated at from 60° to 70° C. The filtrate was concentrated to dryness on a rotary steamer. 612 g (i.e. a yield of 94% of theory) of the stated carboxymethylbetaine mixture according to the invention (with a residual NaCl content of 3.2% by weight and a residual Na glycolate content of 3.1% by weight) were obtained.

Characterization by $^1H$ NMR ($CD_3OD$):

Betaine component of the formula $C_nF_{2n+1}$—CHF—$(CH_2)_2$—$N^+(CH_3)_2$—$CH_2CO_2^-$:
γ-CHF: 5.44 ppm (1H, d, m)
β-$CH_2$: 2.45 ppm (2H, m)
α-$CH_2$: 4.00 ppm (2H, m)
N ($CH_3$)$_2$: 3.36 ppm (6H, s)
$CH_2$—$CO_2^-$: 3.95 ppm (2H, s)

Betaine component of the formula
$C_nF_{2n+1}$—$(CH_2)_3$–$N^+(CH_3)_2$—$CH_2CO_2^-$:
γ-$CH_2$: 2.45 ppm (2H, m)
β-$CH_2$: 2.15 ppm (2H, m)
α-$CH_2$: 3.76 ppm (2H, m)
N ($CH_3$)$_2$: 3.32 ppm (6H, s)
$CH_2$—$CO_2^-$: 3.95 ppm (2H, s)

The perfluoroalkyl radical $C_nF_{2n+1}$ is a mixture of perfluorinated $C_5$, $C_7$, $C_9$ and $C_{11}$ alkyls of the following composition, in area percentages determined by gas chromatography: $C_5$:$C_7$:$C_9$:$C_{11}$=4:59:36:1

The carboxymethylbetaine mixture according to the invention was tested in respect of its effectiveness in lowering the surface tension of water (mN/m) in this context using different concentrations (in percent by weight) in each case at 35° C. The results are summarized below:

| % by weight | mN/m |
| --- | --- |
| 0.1 | 18.1 |
| 0.05 | 19.1 |
| 0.02 | 19.3 |
| 0.01 | 19.5 |

EXAMPLE 11

Preparation of a mixture essentially comprising

80% by weight of $C_nF_{2n+1}$—CHF—$(CH_2)_2$—$N^+(CH_3)_2CH_2CO_2^-$ and

20% by weight of $C_nF_{2n+1}$—$(CH_2)_3$—$N^+(CH_3)_2$—$CH_2CO_2^{-31}$.

$C_nF_{2n+1}$ has the following composition:
$C_5:C_7:C_9:C_{11}=27:56:15:2$

A 4 l stirred apparatus was charged with a mixture of 483.3 g of $C_nF_{2n+1}$—CHF—$(CH_2)_2$—$N(CH_3)_2$ and $C_nF_{2n+1}$—$(CH_2)_3$—$N(CH_3)_2$ in a weight ratio of 80:20 (1.0 mol), 130.8 g of sodium chloroacetate (98% pure, 1.1 mol), 773 g of ethanol and 39 g of water. The reaction mixture was heated at reflux (approximately 80° C.) with stirring for 30 hours. 2.2 g of NaOH were added as a 30% strength aqueous solution over the course of the reaction. When the reaction had finished, the NaCl was substantially removed by filtering over a rapid pressure filter heated at from 60° to 70° C. 1295 g (96% of theory) of a 40% strength solution of the carboxymethylbetaine mixture according to the invention (with a residual NaCl content of 1.9% by weight and a residual amine content of 0.8% by weight, based in each case on the dry product) were obtained. The betaine was characterized as in Example 10.

The carboxymethylbetaine mixture according to the invention was tested with respect to its effectiveness in lowering the surface tension of water (mN/m), in this context using different concentrations (in percent by weight) in each case at 80° C. The results are summarized below:

| % by weight | mN/m |
| --- | --- |
| 0.1 | 14.2 |
| 0.04 | 14.2 |
| 0.02 | 14.9 |
| 0.01 | 14.9 |
| 0.005 | 14.9 |

The mixture of saturated carboxymethylbetaines according to the invention was also tested with respect to its thermal stability and compared with unsaturated carboxymethylbetaine of the formula $C_nF_{2n+1}$—CF=CH—$CH_2$—$N^+(CH_3)_2CH_2CO_2^-$, where $C_nF_{2n+1}$ is as defined. From each test product a 2% by weight strength solution in water/ isopropanol (in a volume ratio of 8:1) as solvent was prepared. The pH of each solution was adjusted to 8 using diethanolamine. The fluoride content of both solutions was also determined, and was <1 ppm. The two test solutions therefore had a pH of 8 and a fluoride content of <1 ppm. These initial solutions were heated to 65° C. and maintained at this temperature. The pH and the fluoride content were determined after 4 and 10 days. The result is summarized below and indicates that the product according to the invention is of substantially greater thermal stability, since both the pH and the fluoride content remain unchanged over the entire test period, in contrast to the comparative product:

|  | 4 days | | 10 days | |
| --- | --- | --- | --- | --- |
|  | pH | Fluoride | pH | Fluoride |
| product of the invention | 8 | <1 ppm | 8 | <1 ppm |
| comparative product | 6.1 | 16 ppm | 5.6 | 24 ppm |

EXAMPLE 12

This example is intended to show that the carboxymethylbetaine mixture according to the invention can also be prepared starting from monochloroacetic acid.

A 1 l stirred apparatus was charged with 320 g of ethanol, 6 g of water and 17.6 g of NaOH prills (0.44 mol), and was then stirred at 50° C. until no more solid NaOH was present. At that point 52 g of 80% strength by weight monochloroacetic acid (0.44 mol) were slowly added dropwise at 50° C. (over about 30 minutes), leading to partial precipitation of sodium chloroacetate in the form of a fine powder. 193 g (0.4 mol) of the mixture of $C_nF_{2n+1}$—CHF—$(CH_2)_2$—$N(CH_2)_2$ and $C_nF_{2n+1}$—$(CH_2)_3$—$N(CH_3)_2$ employed in Example 11 were added in a weight ratio of 80:20, after which the reaction mixture was stirred at 80° C. for 29 hours. 10.6 g of 30% by weight strength aqueous NaOH solution were added over the course of the reaction. When the reaction had finished the reaction mixture was worked up as in Example 11. 524 g (95% of theory) of a 39% strength solution of the carboxymethylbetaine mixture according to the invention (with a residual NaCl content of 2.1% by weight and a residual amine content of 1.2% by weight, based in each case on dry product, were obtained. The betaine was characterized as in Example 10.

EXAMPLE 13

This example is intended to show that the carboxymethylbetaine mixture according to the invention can also be prepared using methyl chloroacetate as carboxymethylating agent.

Preparation of a mixture essentially comprising:

80% by weight of $C_5F_{11}$—CHF—$(CH_2)_2$—$N^+(CH_3)_2$—$CH_2CO_2^-$ and

20% by weight of $C_5F_{11}$—$(CH_2)_3$—$N^+(CH_3)_2$—$CH_2CO_2^-$.

In a 500 ml stirred apparatus, 112.4 g (0.3 mol) of a mixture of 80% by weight of $C_5F_{11}$—CHF—$(CH_2)_2$—$N(CH_3)_2$ and 20% by weight of $C_5F_{11}$—$(CH_2)_3$—$N(CH_3)_2$, 36.7 g (0.3 mol) of Cl—$CH_2$—$CO_2C_2$—$H_5$ and 160 g of ethanol were stirred at 80° C. for 18 hours. Subsequently, 24 g of a 50% by weight strength aqueous NaOH solution (0.3 mol) were added and stirring was continued at 80° C. for 2.5 hours. The NaCl precipitated (14.7 g) was filtered off at from 60° to 70° C. and the filtrate was concentrated to dryness on a rotary evaporator. 107.7 g (i.e. a yield of 81% of theory) of the stated carboxymethylbetaine mixture (with a residual NaCl content of 2.5% by weight) were obtained. The product was characterized by $^1H$ NMR as in Example 10.

Examples 14 and 15 below relate to the mixtures of compounds of the formula (3) and formula (6) according to the invention:

EXAMPLE 14

Preparation of a mixture essentially comprising

80% by weight of $C_nF_{2n+1}$—CHF—$(CH_2)_2$—$N^+(CH_3)_2$—$(CH_2)_3SO_3^-$ and 20% by weight of $C_nF_{2n+1}$—$(CH_2)_3$—$N^+(CH_3)_2$—$(CH_2)_3SO_3^-$.

A 2 l stirred apparatus (fitted with condenser, dropping funnel and thermometer) was charged with 300 g (0.624 mol) of a mixture of 80% by weight of $C_nF_{2n+1}$—CHF—$(CH_2)_2$—$N(CH_3)_2$ and 20% by weight of $C_nF_{2n+1}$—$(CH_2)_3$—$N(CH_3)_2$ and 439 g of monoethylene glycol monobutyl ether (butylglycol) and heated at 60° C. 76.9 g (0.630 mol) of propanesultone were metered into the heated mixture, which was then stirred at from 105° to 110° C. for 40 hours. The reaction mixture was worked up by adding 438 g of water and stirring at 90° C. for 3 hours (hydrolysis of excess propanesultone). The alkylsulfobetaine mixture according to the invention and indicated above was obtained in a yield of 85% of theory.

The statements made in Example 11 apply to the perfluoroalkyl radical $C_nF_{2n+1}$.

The sulfobetaine mixture according to the invention was tested with respect to its effectiveness in reducing the surface tension of water (mN/m), in this context using different concentrations (in percent by weight) in each case at room temperature (20° C.). The results are summarized below:

| % by weight | mN/m |
|---|---|
| 0.1 | 20.4 |
| 0.05 | 20.7 |
| 0.02 | 21.7 |
| 0.01 | 21.7 |

EXAMPLE 15

This example is intended to show that the sulfobetaine mixture according to the invention can also be prepared using butanesultone as sulfoalkylating agent.

Preparation of a mixture essentially comprising

80% by weight of $C_nF_{2n+1}$—CHF—$(CH_2)_2$—$N^+(CH_3)_2$—$(CH_2)_4SO_3^-$ and 20% by weight of $C_nF_{2n+1}$—$(CH_2)_3$—$N^+(CH_3)_2$—$(CH_2)_4SO_3^{-31}$.

The statements made in Example 14 apply to the perfluoroalkyl radical $C_nF_{2n+1}$.

A 250 ml stirred apparatus was charged with 48.1 g (0.1 mol) of a mixture of 80% by weight of $C_nF_{2n+1}$—CHF—$(CH_2)_2$—$N(CH_3)_2$ and 20% by weight of $C_nF_{2n+1}$—$(CH_2)_3$—$N(CH_3)_2$ and 31 g of butylglycol and heated to 110° C. 13.8 g (0.101 mol) of butanesulfone were metered into the heated mixture, which was then stirred at approximately 120° C. for 16 hours. The reaction mixture was worked up by adding 31 g of water and stirring at approximately 95° C. for 5 hours (hydrolysis of excess butanesultone). The sulfobetaine mixture according to the invention was obtained in a yield of 85% of theory.

Example 16 below relates to the mixtures according to the invention essentially comprising the carboxyalkylbetaine mixtures and sulfobetaine mixtures according to the invention:

EXAMPLE 16

50 parts by weight of the carboxymethylbetaine mixture according to the invention of Example 11 (mixture 1) and 50 parts by weight of the alkylsulfobetaine mixture according to the invention of Example 14 (mixture 2) were mixed with stirring at room temperature (mixture 3).

Mixture 3 according to the invention was tested with respect to its effectiveness in reducing the surface tension of water (mN/m) in this context using different concentrations (in % by weight) in each case at room temperature (20° C.). The results are summarized below:

| % by weight | mN/m |
|---|---|
| 0.1 | 17.1 |
| 0.05 | 18.5 |
| 0.02 | 18.5 |
| 0.01 | 18.5 |

We claim:
1. Carboxyalkylbetaines of the formula (2) below

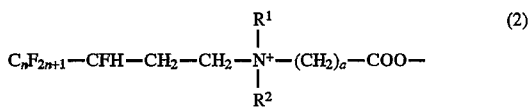

in which a is 1, 2, 3 or 4, n is an integer from 3 to 17 and $R^1$ and $R^2$ are $C_1$ to $C_4$ alkyl, $C_1$ to $C_4$ hydroxyalkyl or hydrogen, with the proviso that only one of the two substituents $R^1$ and $R^2$ is hydrogen.

2. Carboxyalkylbetaine mixtures essentially comprising
A) from 60 to 90% by weight of at least one carboxyalkylbetaine of the formula (2) below

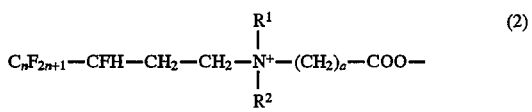

in which a is 1, 2, 3 or 4, n is an integer from 3 to 17 and $R^1$ and $R^2$ are $C_1$ to $C_4$-alkyl, $C_1$ to $C_4$ hydroxyalkyl or hydrogen, with the proviso that only one of the two substituents $R^1$ and $R^2$ is hydrogen, and
b) from 10 to 40% by weight of at least one carboxyalkylbetaine of the formula (5) below

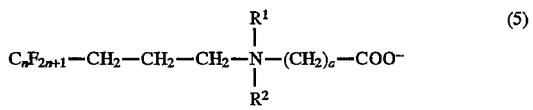

in which a, n, $R^1$ and $R^2$ are as defined, percentages by weight being based on the weight of the mixture.

* * * * *